United States Patent
Someda et al.

(10) Patent No.: US 10,578,587 B2
(45) Date of Patent: Mar. 3, 2020

(54) DETERIORATION DIAGNOSIS METHOD, A DETERIORATION DIAGNOSIS SYSTEM, AND A SENSOR

(71) Applicant: Kabushiki Kaisha Toshiba, Tokyo (JP)

(72) Inventors: Keiichiro Someda, Kanagawa (JP);
Kazuo Watabe, Kanagawa (JP);
Osamu Nishimura, Kanagawa (JP);
Michihiko Inukai, Kanagawa (JP)

(73) Assignee: Kabushiki Kaisha Toshiba, Tokyo (JP)

(*) Notice: Subject to any disclaimer, the term of this patent is extended or adjusted under 35 U.S.C. 154(b) by 237 days.

(21) Appl. No.: 15/691,178

(22) Filed: Aug. 30, 2017

(65) Prior Publication Data

US 2018/0217103 A1    Aug. 2, 2018

(30) Foreign Application Priority Data

Feb. 2, 2017    (JP) ................ 2017-017744

(51) Int. Cl.
*G01N 29/04* (2006.01)
*G01N 29/11* (2006.01)
*G01N 29/07* (2006.01)

(52) U.S. Cl.
CPC ......... *G01N 29/046* (2013.01); *G01N 29/045* (2013.01); *G01N 29/07* (2013.01);
(Continued)

(58) Field of Classification Search
CPC .... G01N 29/046; G01N 29/045; G01N 29/07; G01N 29/11; G01N 2291/0258; G01N 2291/0232
See application file for complete search history.

(56) References Cited

U.S. PATENT DOCUMENTS 4,926,691 A * 5/1990 Franklin ............... G01H 13/00
703/2
5,621,172 A    4/1997 Wilson et al.
(Continued)

FOREIGN PATENT DOCUMENTS

JP    3-72352    7/1991
JP    5-126804   7/1991
(Continued)

OTHER PUBLICATIONS

Extended European Search Report issued by the European Patent Office dated Jan. 4, 2018, in European Patent Application No. 17187206.2.

(Continued)

*Primary Examiner* — Freddie Kirkland, III
(74) *Attorney, Agent, or Firm* — Finnegan, Henderson, Farabow, Garrett & Dunner, L.L.P.

(57) ABSTRACT

According to one embodiment, a method is used for diagnosing a deterioration of a utility pole having at least one bolt and a plurality of holes provided for attaching the bolt. In the method, an impact is applied to the bolt. Elastic waves generated due to the impact are detected by a sensor shaped like a bolt. The sensor is attached to at least one of the holes. A propagation situation of the elastic waves in the utility pole is derived, based on the elastic waves detected, and each position of the bolt and the sensor.

19 Claims, 8 Drawing Sheets

(52) U.S. Cl.
CPC ..... *G01N 29/11* (2013.01); *G01N 2291/0232* (2013.01); *G01N 2291/0258* (2013.01)

(56) References Cited

U.S. PATENT DOCUMENTS

| | | | |
|---|---|---|---|
| 5,792,960 A * | 8/1998 | Lewis | G01N 3/00 |
| | | | 73/786 |
| 6,813,948 B1 | 11/2004 | Rinn | |
| 9,267,925 B2 * | 2/2016 | Bartuli | G01N 29/12 |
| 2014/0069192 A1 | 3/2014 | Bartuli et al. | |
| 2018/0348169 A1 * | 12/2018 | Lee | G01N 29/11 |

FOREIGN PATENT DOCUMENTS

| | | |
|---|---|---|
| JP | 11-37744 | 2/1999 |
| JP | 2001-289830 | 10/2001 |
| JP | 2002-345132 | 11/2002 |

OTHER PUBLICATIONS

Krause et al., "Elastic wave modes for the assessment of structural timber: ultrasonic echo for building elements and guided waves for pole and pile structures," J. Civil Struct. Health Monit. (2015), 5:221-249.

* cited by examiner

DETERIORATION DIAGNOSIS METHOD, A DETERIORATION DIAGNOSIS SYSTEM, AND A SENSOR

CROSS-REFERENCE TO RELATED APPLICATION

This application is based upon and claims the benefit of priority from Japanese Patent Application No. 2017-017744, filed on Feb. 2, 2017; the entire contents of which are incorporated herein by reference.

FIELD

Embodiments described herein relate generally to a deterioration diagnosis method, a deterioration diagnosis system, and a sensor.

BACKGROUND

As non-destructive deterioration diagnosis method for a prestressed concrete utility pole, an electrode is connected to an edge position of a tension bar thereof, a counter electrode is contacted on a side face of a position to be inspected, and an amount of moisture in the concrete is estimated from the impedance characteristic. Thus, a hydrogen concentration in the steel material is estimated as a standard for brittle fracture of the tension bar. In this method, the electrode needs to contact near the position to be inspected. Accordingly, in order to inspect all regions of the utility pole, all surfaces of the utility pole needs to be scanned by the electrode, and burden for the inspection is very large.

As another method, velocity tomography method is well known. In this method, elastic waves are occurred by striking a predetermined portion of the concrete, the elastic waves (propagated inside the concrete) are detected by an elastic wave sensor (AE sensor), and a distribution of elastic wave velocity (as a standard for deterioration and damage position inside the concrete) is estimated from a travel time of the elastic waves to the sensor. In the velocity tomography method, an adhesion is mainly used to attach the sensor. However, the adhesion is hard to attach and remove a plurality of sensors in a short time. Furthermore, in the case of fixing such as binding a measurement target with a band, the pressure-bonding force has dispersion, and the elastic waves cannot be suitably detected. Furthermore, in order to analyze the distribution of elastic wave velocity, an excitation position and an attachment position of AE sensor need to be correctly determined. However, the target position is not previously determined. Accordingly, the excitation position and the attachment position cannot be correctly determined.

DETAILED DESCRIPTION

Figure 1A:
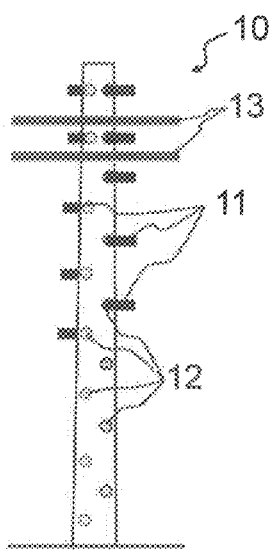
FIGS. 1A and 1B are one example of a deterioration diagnosis system according to the first embodiment.

According to on embodiment, a method is used for diagnosing a deterioration of a utility pole having at least one belt and a plurality of holes provided for attaching the bolt. In the method, an impact is applied to the bolt. Elastic waves generated due to the impact are detected by a sensor shaped like a bolt. The sensor is attached to at least one of the holes. A propagation situation of the elastic waves in the utility pole is derived, based on the elastic waves detected, and each position of the bolt and the sensor.

Hereinafter, the deterioration diagnosis method, the deterioration diagnosis system and the sensor according to embodiments are described below with reference to drawings. Having the same reference numeral means the same component. Incidentally, the drawings are schematic or conceptual, a relationship between the thickness and width of each part, the dimensional ratio between parts, etc. are not necessarily the same as actual ones. Furthermore, even the same part may be depicted in the different dimensions or dimensional ratio among the drawings.

The First Embodiment

Figure 1B:
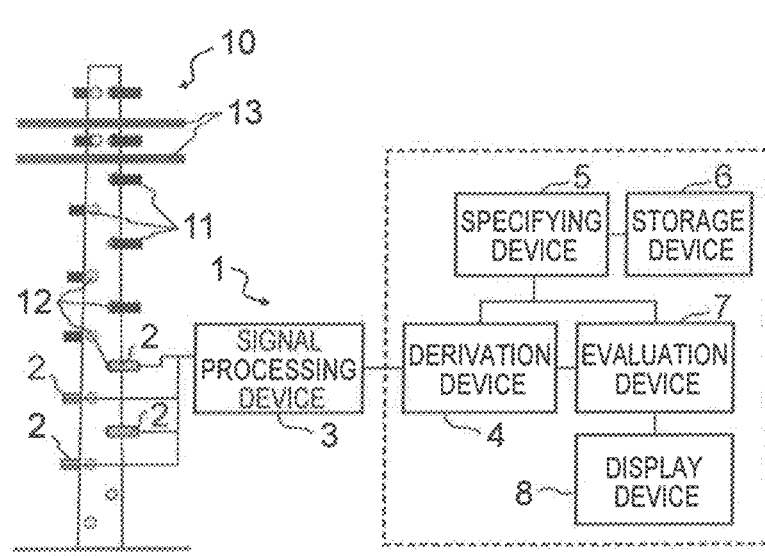

The first embodiment will be explained by referring to FIGS. 1A and 1B. FIGS. 1A and 1B show one example of the deterioration diagnosis system according to the first embodiment.

FIG. 1A shows a utility pole as a diagnosis target. As shown in FIG. 1A, the utility pole 10 (diagnosis target for deterioration diagnosis system) is a columnar concrete structure almost vertically installed on a ground (such as road or sidewalk). In general, the utility pole 10 has a hollow structure inside, and shaped by covering a steel framing with concrete. On the utility pole 10, a plurality of holes 12 is provided for attaching a bolt as a footing for a worker (user) to inspect. A female screw is threaded to each of the holes 12, and a male screw is threaded to the bolt 11. By engaging the female screw with the male screw, the bolt 11 is fixed to the utility pole 10. Instead of each of the holes 12, a nut having a female screw threaded may be embedded into the utility pole 10. Each position of the holes 12 (previously provided on the utility pole 10) is designedly determined. For example, the holes 12 are provided with staggered form at a predetermined interval along axis direction of the utility pole 10. Normally, the bolt 11 of the utility pole 10 is not attached to the holes 12 positioned near the ground. They are attached to the holes 12 having a height (from the ground) at which a person cannot reach (e.g., larger than 180 cm). At the holes 12 (of the utility pole) near the ground, in general, the bolt 11 as a footing used for inspection if necessity is attached. A range of the holes 12 (of the utility pole) to which the bolt 11 is not attached is called as "lower part of the utility pole". Furthermore, a range of the holes 12 (of the utility pole) to which the bolt 11 is attached is called as "upper part of the utility pole". At the upper part of the utility pole 10, an electric wire is attached.

Next, the deterioration diagnosis system 1 of the first embodiment will be explained. FIG. 1B shows a situation that the deterioration diagnosis system 1 is installed to the utility pole 10. As shown in FIG. 1B, the deterioration diagnosis system 1 includes a sensor 2, a signal processing device 3, a derivation device 4, a specifying device 5, a storage device 6, an evaluation device 7, and a display device 8. The sensor 2 is attached using the holes 12 positioned at the lower part of the utility pole 10, and outputs a voltage signal by detecting elastic waves occurred due to an impact applied. The signal processing device 3 processes the voltage signal, and outputs an elastic wave signal. The derivation device 4 derives a propagation velocity of the elastic wave in the utility pole by inputting the elastic wave signal, and derives a distribution of propagation velocity at each position in the utility pole. The specifying device 5 specifies a threshold and so on. The storage device 6 stores position information of the holes of the utility pole and information of the bolt. The evaluation device 7 evaluates a deterioration region in the utility pole by comparing the distribution of propagation velocity with the threshold. The display device 8 displays an evaluation result by the evaluation device 7.

By applying an impact to the bolt 11 attached to the hole 12 positioned at the upper part of the utility pole 10, an elastic wave occurs. In the deterioration diagnosis system 1, the sensor 2 detects the elastic wave, and a distribution of propagation velocity of the elastic wave is derived. As a result, deterioration in the utility pole is diagnosed.

By applying an impact to the bolt 11 attached to the hole 12 (of which position is previously known) at the upper part of the utility pole 10, a position where the impact is applied is easily known. Furthermore, by detecting the elastic wave by the sensor attached to the hole 12 (of which position is previously known) at the lower part of the utility pole 10, in the case of analyzing by the derivation device 4, a position of the sensor is accurately detected, and analysis accuracy can be improved.

Figure 2A:
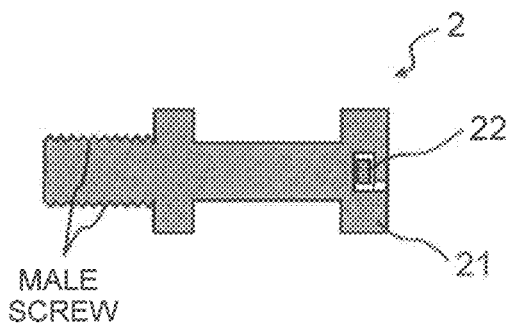
FIGS. 2A, 2B and 2C are sectional views showing one example of a sensor included in the deterioration diagnosis system according to the first embodiment.
Figure 2B:
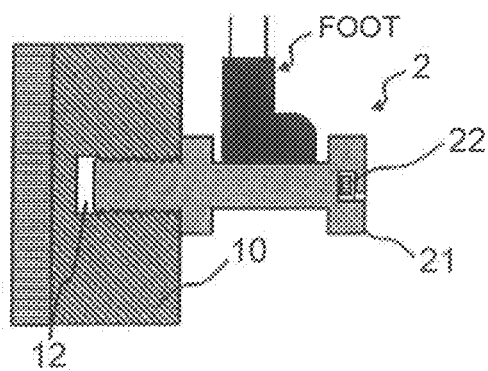

First, the sensor 2 will be explained. FIG. 2A shows a sectional view of one example of the sensor 2. As shown in FIG. 2A, the sensor 2 equips a housing 21 and a detector 22. The housing 21 is formed as bolt-shape. The detector 22 is installed to the housing 21. On the housing 21, a male screw is formed so as to be tightly attached into the hole of the utility pole. By engaging the male screw of the housing with the female screw of the utility pole, the sensor 2 is fixed to the utility pole. Preferably, a shape of the housing 21 is almost same as a shape of the bolt 11. After attaching the sensor to the utility pole 10, the sensor is used as a footing for the worker. FIG. 2B shows one example that the sensor 2 attached into the hole 12 of the utility pole is used as the footing. As a material of the housing 21, a metal such as steel is preferred. The utility pole is mainly shaped with the concrete. Accordingly, in a frequency band including a major component of the elastic wave propagating inside the utility pole, so long as it is a hard material for the elastic wave to propagate without attenuation and easy to process, any material can be used.

The detector 22 is installed into the housing 21, and a part to detect elastic wares occurred due to the impact. For example, the detector 22 mainly detects acceleration component of the elastic waves. As the detector 22, AE (Acoustic Emission) sensor, acceleration sensor, or vibration sensor, is used. If a velocity tomography analysis method is used as a method for diagnosing deterioration, AE sensor had better be used. In the velocity tomography analysis method, by evaluating a distribution of propagation velocity of elastic waves (diagnosis target), a position and a degree of deterioration (or damage) which is latent in the diagnosis target are estimated.

The detector 22 converts the detected elastic waves to a voltage signal. The detector 22 performs processing such as amplification and frequency-limitation to the voltage signal, and outputs the processed voltage signal to the signal processing device 3.

An installation position of the detector 22 may be a surface of the housing 21, or built in the housing.

Figure 2C:
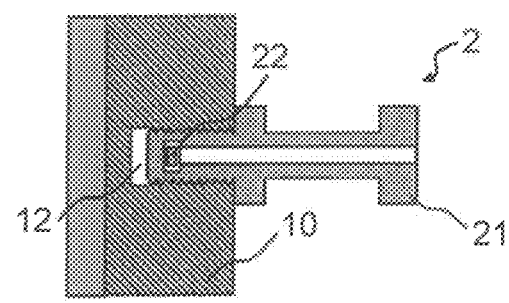
Figure 2C:
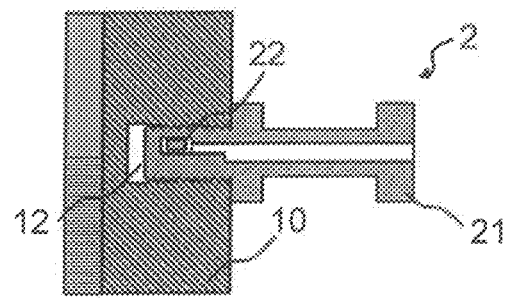
Figure 2C:
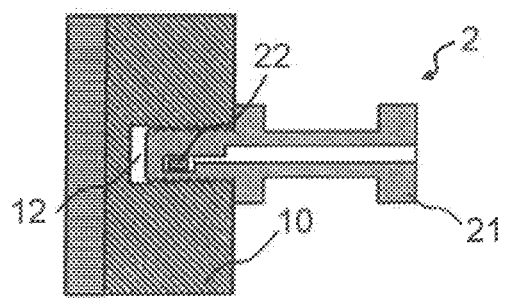

FIG. 2C shows a sectional view of one example of the case that the sensor 2 (the detector 22 is installed inside a male screw part of the housing 21) is attached to the utility pole 10. By installing the detector 22 inside a part where a male screw of the housing 21 is formed, if the sensor 2 is attached to the hole 12 of the utility pole 10, the detector 22 is entered inside the utility pole 10, accuracy to detect the elastic waves can be improved.

Furthermore, the detector 22 often includes a detection face to detect the elastic waves with high sensitivity.

Under the condition that the sensor is attached to the utility pole, the detection face of the detector 22 is preferably located so as to face a propagation direction of the elastic wave. As shown in FIG. 2C, a direction to install the detector 22 can be variously thought out.

A plurality of sensors is preferably installed into holes 12 of the utility pole. By using one sensor 2, deterioration diagnosis of the utility pole can be performed. However, in order to diagnose with higher accuracy, a plurality of sensors 2 had better be used. For example, among a plurality of holes of the utility pole, each sensor is preferably installed into about four holes.

In general, the sensor 2 is installed into the hole 12 placed at a lower part of the utility pole 10. The reason is already mentioned, i.e., the bolt 11 is not attached to the hole 12 positioned at the lower part of the utility pole. The sensor (detector) is connected to the signal processing device 3 via wiring. However, connection therebetween is not limited to wiring. Information detected by the sensor 2 can be communicated by not only a wire but also a radio. In this case, a power source device and a transmitting device (it is also called as "output device") to transmit the information are separately installed to the sensor 2.

Next, the signal processing device 3 will be explained. The signal processing device 3 inputs a voltage signal outputted from the sensor 2. By performing signal processing (such as noise-reduction, parameter-extraction) to the voltage signal inputted, the signal processing device 3 extracts characteristics including information related to elastic waves. For example, the information related to elastic waves is amplitude, energy, rise time, duration, frequency and zero-crossing count of the voltage signal. The signal processing device 3 outputs information based the extracted characteristics (as an elastic wave signal) to the derivation device 4. The elastic wave signal (outputted by the signal processing device 3) includes an ID of the sensor, detection time, signal amplitude, energy, rise time, duration, and frequency of the elastic waves.

Here, for example, the amplitude of the voltage signal is a value of maximum amplitude among the elastic waves. The energy is a time-integrated value of the amplitude squared at each timing. Definition of the energy is not limited to above example. By using envelop of the waveform, the voltage signal may be approximated. The rise time is, for example, a lapse of time of the elastic wave from start timing (the elastic value is equal to zero-value) to rise timing (the elastic wave is over a predetermined value). The duration is, for example, a lapse of time from the rise timing (the elastic wave is over the predetermined value) to timing when the amplitude is below a predetermined value. The frequency is a frequency of the elastic wave. The zero-crossing count is, for example, the number of times that the elastic wave is crossing a reference line passing zero-value.

The signal processing device 3 equips, for example, a CPU (Central Processing Unit), a memory and an auxiliary memory, and executes an evaluation program. Moreover, all or a part of the signal processing device 3 may be realized using hardware such as ASIC (application Specific Integrated Circuit, PLD (Programmable Logic Device), or FPGA (Field Programmable Gate Array).

The signal processing device 3 is connected to the sensor 2 via a wire (wiring) or a radio. In the case of connecting via radio, a receiving device to receive information transmitted from the sensor is equipped. Furthermore, the signal processing device 3 may be built in the senses 2. The signal processing device and the sensor may be called as "sensor unit".

Next, the derivation device 4 will be explained. The derivation device 4 inputs an elastic wave signal outputted from the signal processing device 3. Furthermore, the derivation device 4 needs to acquire a sensor-position information related to a sensor ID in advance. In the deterioration diagnosis system of the first embodiment, as mentioned-above, position information of the hole 12 of the utility pole is previously known. Accordingly, position information of the sensor 2 (attached to the hole 12 of the utility pole) and the sensor ID can be easily acquired. Furthermore, a travel time from timing when an impact is applied to timing when the elastic wave arrives at each sensor 2 needs to be acquired. Here, for example, the worker applies an impact to the bolt 11 (previously installed into the hole of the utility pole) by hammering. Accordingly, position information of the bolt 11 (to which the impact is applied) and the travel time can be easily acquired. Specifying correspondence relation of the sensor ID to a position of the hole of the utility pole, and a position of the bolt to be applied with impact, are performed by the specifying device (explained afterwards). A time when the impact is applied may be actually measured by the worker. For example, by installing the acceleration sensor to a material for hammering, a time when the impact is applied may be measured. Moreover, as the material to apply the impact, a hard material (such as metal) is preferable to a soft material. As this reason, high acceleration (G value) is acquired from the hard material.

Even if the impact is applied to only one bolt 11, deterioration diagnosis in the utility pole can be performed. However, in order to diagnose with higher accuracy, the impact is preferably applied to many bolts 11 (for example, about ten bolts).

Based on the sensor ID included in the elastic wave signal inputted, travel time information as a difference between a time when the impact is applied and a time when the elastic wave is detected by the sensor, and position information of the bolt and the sensor, the derivation device 4 derives a distribution of propagation velocity of the elastic wave. The distribution of propagation velocity is a distribution representing a propagation velocity of the elastic wave at a predetermined part in the utility pole. For example, by using the velocity tomography analysis method, the derivation device 4 derives the distribution of propagation velocity of the elastic wave in the utility pole. In the velocity tomography analysis method, an elastic wave occurred due to the impact (applied to a structure) is detected by a plurality of AE sensors, a propagation velocity of an analysis model of the structure is corrected so that an error between a theoretical travel time (from the application position of the impact to each sensor) and a measured travel time converges within an allowable value. In this way, the distribution of propagation velocity of the elastic wave in the structure is acquired. The larger the deterioration degree of the structure is, the lower the propagation velocity of the elastic wave (propagating inside the structure) is. Accordingly, by using the velocity tomography analysis method, a degree of inner deterioration of the structure can be evaluated from the distribution of propagation velocity of the elastic wave.

In the velocity tomography analysis method, analysis is performed based on a propagation time (travel time) of the elastic wave from the application position of the impact to the detection position of the elastic wave by the sensor. However, analysis method is not to this. For example, attenuation tomography analysis method (for analyzing based on attenuation amount of amplitude of the elastic wave from the application position of the impact to the detection position by the sensor) may be used. In the attenuation tomography analysis method, the larger the deterioration degree of the structure is, the larger the attenuation amount of amplitude of the elastic wave (propagating inside the structure) is. Accordingly, a degree of inner deterioration of the structure can be evaluated from the distribution of attenuation amount of amplitude of the elastic wave. Moreover, in the attenuation tomography analysis method, the elastic wave (occurred when the impact is applied) needs to be acquired. By locating a sensor adjacent to the bolt to be applied with the impact, the elastic wave may be acquired. Alternatively, by applying the impact to the sensor, the elastic wave may be acquired.

The propagation time (travel time) of the elastic wave in the velocity tomography analysis method, and the attenuation amount of amplitude of the elastic wave in the attenuation tomography analysis method, are one example of characteristics information of the elastic wave reflecting a degree of deterioration (or damage) inside the structure. This information is generically called "propagation situation".

For example, the derivation device 4 equips a CPU, a memory or an auxiliary memory connected to a bus, and executes an evaluation program. By executing the evaluation program, the distribution of propagation velocity of the elastic wave is acquired. Moreover, all or a part of the derivation device may be realized using hardware such as ASIC, PLD or FPGA. As the auxiliary memory, a magnetic disk such as a hard disk, or a semiconductor memory, can be used.

Next, the specifying device 5 will be explained. The specifying device 5 is connected to the derivation device 4 and the evaluation device 7 (explained afterwards). Furthermore, the storage device 6 (explained afterwards) is connected to the specifying device 5. The worker specifies a threshold of the propagation velocity of the elastic wave, a position of the hole (to which the sensor is attached) of the utility pole, a position of the hole (to which the bolt (to be applied with impact) is attached) of the utility pole, the predetermined number of application of impact, and so on (there are called as "parameter information"), via the specifying device 5. The threshold of the propagation velocity can be suitably specified based on situation of the utility pole for the worker to desirably diagnose. For example, as to the utility pole which progress of deterioration is not notable by visual observation, or as to the utility pole having short age of building, the threshold had better be set highly. Furthermore, as to the utility pole which progress of deterioration is notable by visual observation, or as to the utility pole having long age of building, the threshold had better be set lowly. Furthermore, based on diagnosis data or experiential rule in the past, or based on fundamental examination data for sample of similar concrete material, the threshold may be specified. The threshold specified by the worker is outputted to the evaluation device 7. Based on the specified position of the hole of the utility pole 10, precise position information of the hole, and shape information of the bolt and the sensor, are acquired from the storage device 6, and outputted to the derivation device 4. In the case of specifying a plurality of sensors 2, each position of a plurality of holes (to be targeted) of the utility pole is specified by the specifying device 5. Furthermore, in the case of applying the impact to a plurality of bolts 11, whenever the impact is applied, a position of the hole (to which the bolt (to be applied with impact) is attached) of the utility pole is specified.

Specifying parameter information by the specifying device 5 may be performed using an external terminal (such as PC or cellular-phone), or may be directly inputted by attaching a monitor or a touch panel thereto. If the parameter information is specified by the external terminal, transfer of data is executed using Internet, Wi-Fi, or Bluetooth. If the specifying device 5 is composed as the touch panel, and if various parameters are specified thereby, for example, by touching a position of the related hole among holes (of the utility pole) displayed on the panel, the parameter information may be specified. Furthermore, if an ID is assigned to each position of holes (of the utility pole) displayed on the panel, by inputting the ID, the parameter information may be specified.

next, the storage device 6 will be explained. The storage device 6 is connected to the specifying device 5. The storage device 6 stores information related to the utility pole 10. For example, position information of the hole 12 from a predetermined reference in the utility pole 10, information related to physical property (such as material, weight, density) of the bolt 11 and the sensor 2, position information of the detector 22 from a predetermined reference in the sensor 2, are stored. The position information of the hole 12 and the hole ID may be stored with linking. Furthermore, the storage device 6 may be included in the specifying device 5.

As the storage 6, for example, a tape system such as a magnetic tape or a cassette tape, a disk system such as a magnetic disk (floppy disk (registered trade mark)/hard disk) or an optical disk (CD-ROM/MO/MD/DVD/CD-R), a card system such as an IC card (including a memory card) or an optical card, and a semiconductor memory system such as a mask ROM/EPROM/EEPROM/flash ROM, can be used.

Next, the evaluation device 7 will be explained. The evaluation device 7 inputs the distribution of propagation velocity of elastic wave (outputted from the derivation device 4) and the threshold (outputted from the specifying device 5). Based on the distribution of propagation velocity of elastic wave and the threshold, the evaluation device 7 evaluates a deterioration situation of the utility pole. The evaluation device 7 displays an evaluation result via the display device 8.

Based on the threshold related to the propagation velocity of elastic wave, the evaluation device 7 classifies the inputted distribution of propagation velocity into two regions, i.e., a region having high propagation velocity, and a region having low propagation velocity. Specifically, by binarizing the distribution of propagation velocity based on the threshold, the evaluation device 7 classifies into two regions.

Figure 3:
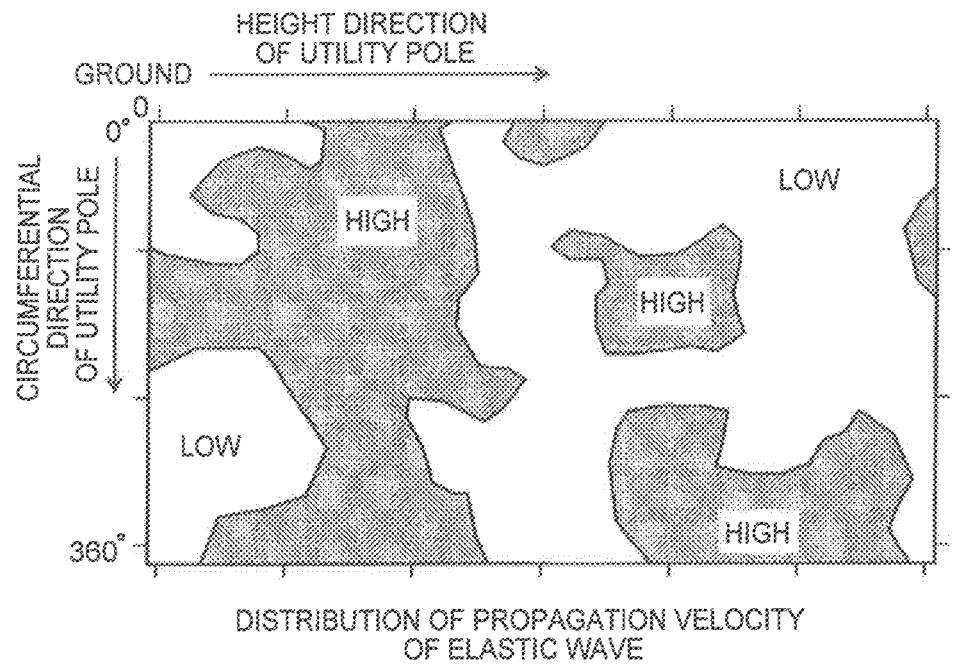
FIG. 3 is an expansion view of a utility pole showing one example of region-classification result by a propagation velocity of elastic waves according to the first embodiment.

FIG. 3 is an expansion view of the utility pole showing one example of region-classification result of the propagation velocity. As shown in FIG. 3, a region having high propagation velocity and a region having low propagation velocity are represented.

In general, as to an elastic wave passing through a region where deterioration has progressed in the utility pole, in comparison with a region where deterioration has not progressed, a propagation velocity of the elastic wave lowers. Accordingly, the region having low propagation velocity of elastic wave is evaluated as a region where deterioration has progressed in the utility pole. The region having high propagation velocity of elastic wave is evaluated as a region where deterioration has not progressed in the utility pole.

Figure 4:
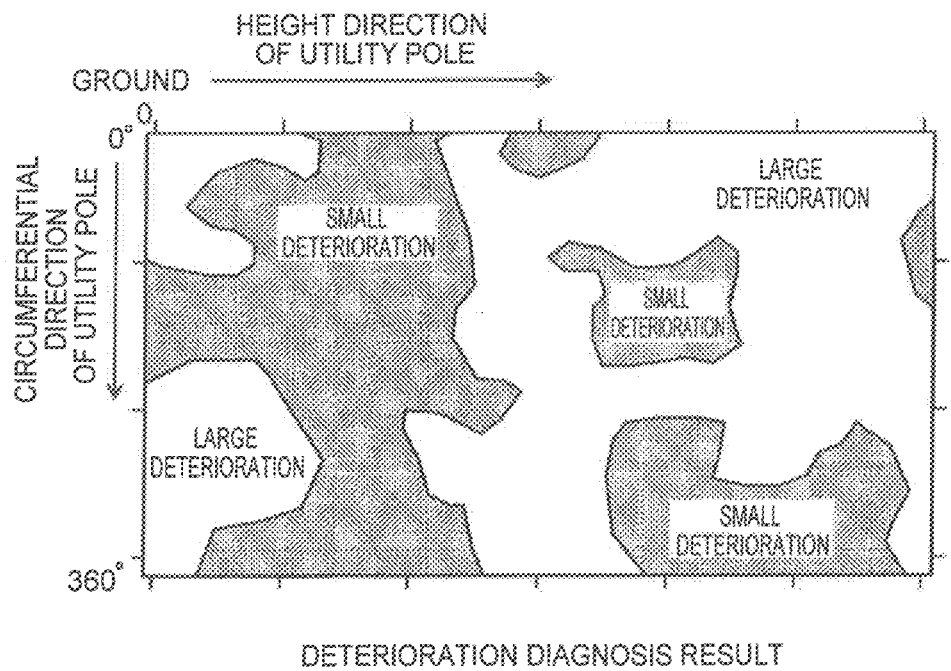
FIG. 4 is one example of an evaluation result by an evaluation device included in the deterioration diagnosis system according to the first embodiment.

FIG. 4 is one example of the evaluation result by the evaluation device 7. As shown in FIG. 4, the region where deterioration has progressed is recognized at a glance.

The evaluation result by the evaluation device 7 is not limited to binarization into the region having low propagation velocity and the region having high propagation velocity. For example, by using the threshold as a reference, multi-stages each having a predetermined range may be set to the propagation velocity, such as "region having very low velocity", "region having low velocity", "region having little low velocity", and so on. Based on the multi-stages, the degree of deterioration may be classified into "limit deterioration", "deterioration", "slight deterioration", and so on.

For example, the evaluation device 7 equips a CPU, a memory or an auxiliary memory, and executes an evaluation program. Moreover, all or a part of the evaluation device may be realized using hardware such as ASIC, PLD or FPGA. Furthermore, processing of the signal processing device 3, the derivation device 4, and the evaluation device 7, may be realized by the same chip.

Next, the display part 8 will be explained. The display device 8 displays the evaluation result by the evaluation device 7. The display device 8 is an image display device such as a liquid crystal display, an organic EL (Electro Luminescence) display, and so on. The display device 8 displays the evaluation result according to control of the evaluation device 7. The display device 8 may be an interface to connect the image display device with the evaluation device 7. In this case, the display device generates a video signal to display the evaluation result, and outputs the video signal to the image display device connected thereto. Furthermore, instead of the display device 8, the specifying device 5 may display the evaluation result.

Next, processing flow of the deterioration diagnosis method of the first embodiment will be explained in detail.

Figure 5:
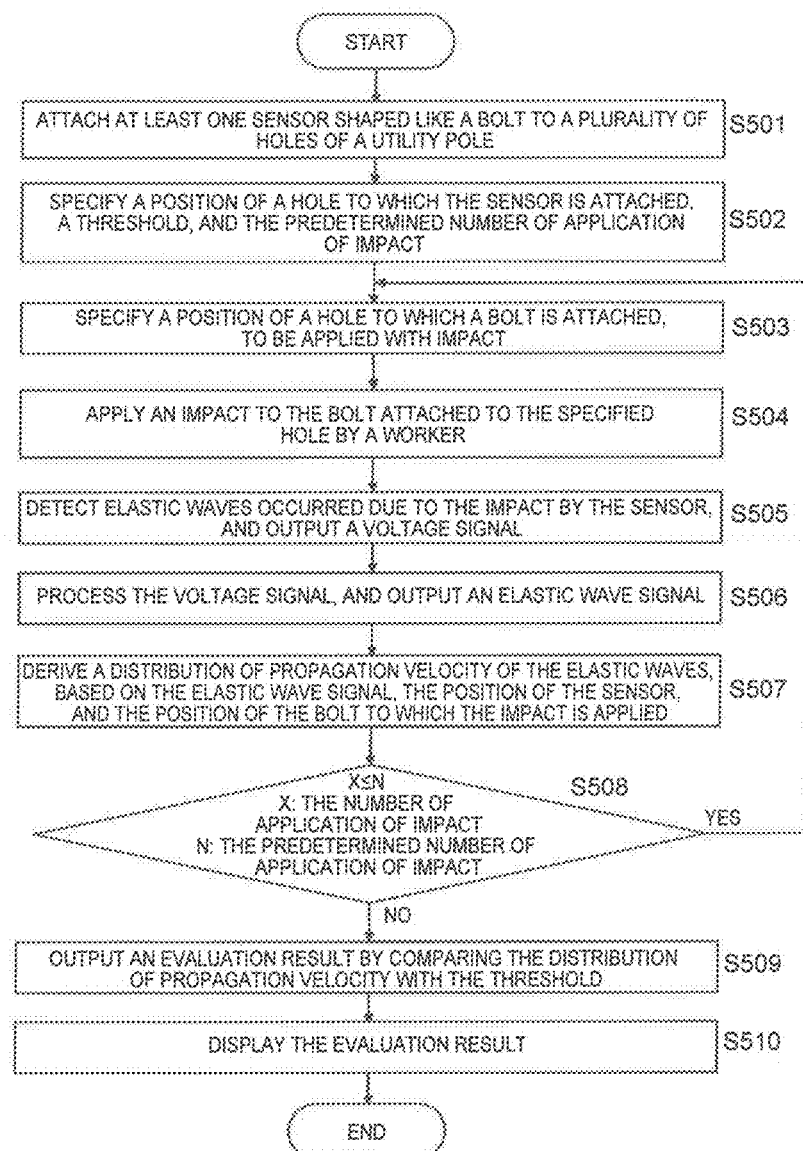
FIG. 5 is a flow chart of processing of a deterioration diagnosis method according to the first embodiment.

FIG. 5 is a flow chart of processing of a deterioration diagnosis method according to the first embodiment. Here, the case of applying the impact N times will be explained.

First, at least one sensor 2 (shaped like a bolt) is attached to any of a plurality of holes 12 of the utility pole 10 as deterioration diagnosis target (S501).

A position of the hole (to which the sensor 2 is attached) of the utility pole 10, and the predetermined number of application of impact (N times), are specified by the specifying device 5. Furthermore, a threshold for propagation velocity of elastic wave is specified (S502).

A position of the hole (to which the bolt 11 (to be applied with impact by the worker) is attached) of the utility pole 10 is specified by the specifying device 5 (S503).

The worker applies an inspect to the bolt attached to the hole placed at the position specified by the specifying device 5 (S504).

An elastic wave (occurred due to the impact) propagating inside the utility pole is detected by the sensor 2, and a voltage signal is outputted (S505).

The voltage signal is processed by the signal processing device 3, and an elastic wave signal is outputted (S506).

Based on the elastic wave signal, position information of the sensor 2 and the hole 12 of the bolt 11 (to which the impact is applied), a distribution of propagation velocity of the elastic wave is derived by the derivation device 4 (S507).

Next, assume that the number of application of impact (actually performed) is X. If "X≤N" is Yes, processing is returned to S503, and processing of S503~S507 is repeated. In this case, when a position of a hole (to which the bolt is attached) of the utility pole 10 is specified at S503, the position of the same holes may be specified. Alternatively, a position of different hole (to which another bolt 11 is attached) may be specified. Furthermore, when a distribution of propagation velocity of the elastic wave is derived at S507, an elastic wave newly acquired and a position information of the hole 12 of the bolt 11 (to which the impact is applied), are added. Based on information accumulated by repeating S503~S507, the derivation device 4 derives a distribution of propagation velocity of elastic wave again. If "X≤N" is No, processing is forwarded to S509 (S508).

By comparing the distribution of propagation velocity with the threshold, the evaluation device 7 binarizes the distribution into a region where deterioration has progressed and a region where deterioration has not progressed, and outputs an evaluation result. As mentioned-above, the evaluation result is not limited to binarization (S509).

The display device 8 displays the evaluation result by the evaluation device 7 (S510). After S510, processing is completed.

At S504, the worker directly applies an impact to the bolt 11. However, the impact may be applied using an impact application device. In this case, the impact application device may have simple component only able to apply the impact to the bolt.

At S508, the processing may be repeated according to the worker's decision. If the impact application device is used, the impact application device repeatedly applies the impact until the predetermined number of application of impact (specified by the specifying device 5) is satisfied.

In the deterioration diagnosis method, the deterioration diagnosis system and the sensor according to the first embodiment, the sensor 2 (shaped like a bolt) is only attached to the hole 12 of the utility pole. As a result, attaching and removing of the sensor 2 can be easily performed.

Furthermore, by using the hole 12 (to attach the bolt 11) previously determined in design of the utility pole, a position where the impact is applied and a position where the sensor 2 is attached can be precisely determined without measurement thereof.

Furthermore, when the distribution of propagation velocity of elastic wave is derived, it is derived based on precise position where the impact is applied and precise position where the sensor 2 is attached. As a result, analysis accuracy can be improved.

Furthermore, by engaging a male screw (threaded onto the sensor 2) with a female screw (threaded into the hole 12 of the utility pole), they are fired. As a result, the sensor 2 can be tightly fixed, and the elastic wave signal can be suitably detected.

Furthermore, by using the sensor 2 shaped like a bolt, the sensor 2 can be used as a footing for the worker.

Furthermore, a shape of the bolt 11 attached to the utility pole is previously known. As a result, the elastic wave including a large number of frequency component according to the natural frequency of the bolt 11 can be detected.

In above explanation, the sensor is attached to holes 12 at the lower part of the utility pole, and an impact is applied to the bolt 11 attached to holes at the upper part of the utility pole. However, by removing the bolt 11 attached to the upper part, in place of the bolt 11, the sensor 2 may be attached to the hole at the upper part. In this case, by attaching a bolt 11 to the hole 12 at the lower part of the utility pole, an impact may be applied to the bolt 11.

In above explanation, the threshold is previously specified by the user. However, the threshold may be automatically set. In this case, by linking the distribution of propagation velocity of the utility pole (inspected in the past) with the threshold, a plurality of thresholds linked to respective distributions is stored into a database. By using this database, the threshold had better be automatically set. For example, the distribution of propagation velocity (derived by the derivation device 4) is compared with respective distributions of propagation velocity stored in the database. Among the respective distributions stored in the database, one distribution moat similar to the distribution (derived by the derivation device 4) is selected, and the threshold used for the selected distribution is also used for the distribution (derived by the derivation device 4). In order to decide similarity between distributions, correlation coefficients may be calculated, or general machine learning may be used. The machine learning is logic constructed using an algorithm to solve a sorting problem. As this algorithm, decision tree, Random forest, SVM (Support Vector Machine), and neural net, are used. By combining these, an algorithm to be used may be created. As a result, even if the worker does not specify the threshold, the threshold can be automatically specified in the system.

In the diagnosis deterioration system of the first embodiment, the derivation device 4 and the evaluation device 7 may be included in a server apart from the utility pole to be inspected. In this case, for example, a sensor unit is attached to a hole of the utility pole, and the worker specifies parameter information via the specifying device. Information of the sensor unit and the specifying device is transmitted to the server by radio. Furthermore, an evaluation result evaluated in the server is transmitted to the specifying device by radio. As a result, the worker can face the utility pole (to be worked) by having only the sensor unit and the specifying device. Accordingly, the worker's burden can be reduced.

The Second Embodiment

Figure 6:
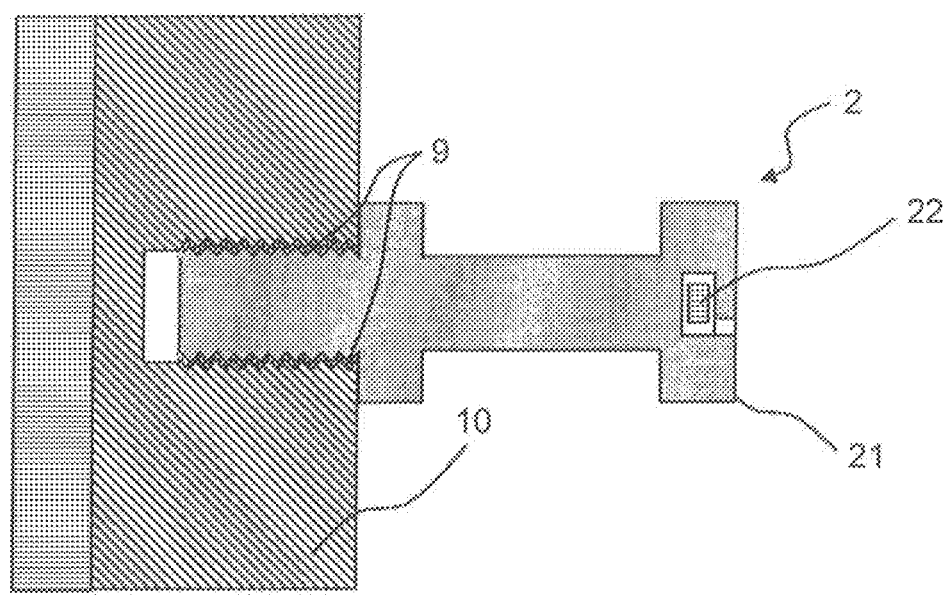
FIG. 6 is one example of a sensor included in the deterioration diagnosis system according to the second embodiment.

The second embodiment will be explained by referring to FIG. 6. FIG. 6 is one example of the sensor 2 included in the deterioration diagnosis system according to the second embodiment. In the deterioration diagnosis method and the deterioration diagnosis system of the second embodiment, when the sensor 2 is attached to the hole 12 of the utility pole, a coupling agent 9 is coated to a gap between the sensor 2 and the hole 12, which is different from the first embodiment. Other components are same as those of the first embodiment.

The coupling agent 9 improvers adhesion between the sensor 2 and the hole 12. By using the coupling agent 9, sensitivity for the sensor 2 to detect the elastic wave can be raised. As the coupling agent 9, a rubber, a filler, a silicon system, an epoxy resin, or a polyester resin, are used.

Furthermore, the coupling agent 9 can be coated to a gap not only between the sensor 2 and the hole 12 of the utility pole but also between the bolt 11 and the hole 12 of the utility pole. The coupling agent is also called as "sealing agent".

Figure 7:
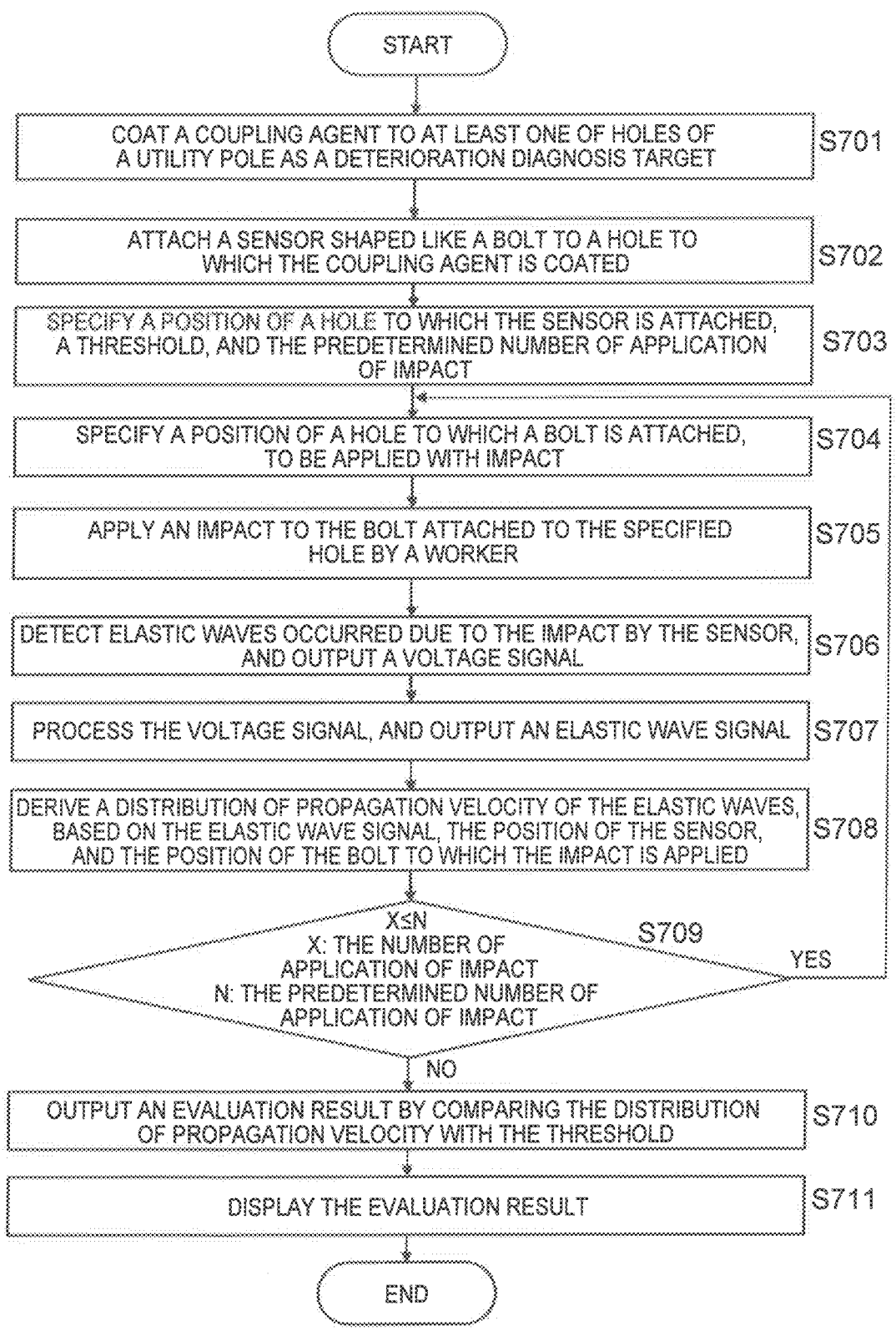
FIG. 7 is a flow chart of processing of the deterioration diagnosis method according to the second embodiment.

FIG. 7 is a flow chart of processing of the deterioration diagnosis method in the case of using the coupling agent 9.

First, the coupling agent 9 is coated to at least one of a plurality of holes 12 of the utility pole as deterioration diagnosis target (S701).

The sensor 2 (shaped like a bolt) is attached to the hole 12 (on which the coupling agent 9 is coated) of the utility pole (S702).

A position of the hole (to which the sensor is attached) of the utility pole, and the predetermined number of application of impact (N times), are specified via the specifying device 5. Furthermore, a threshold for the propagation velocity of elastic wave is specified (S703).

The worker specifies a position of the hole (to which the bolt 11 (to be applied with an impact) is attached) of the utility pole via the specifying device 5 (S704).

The worker applies the impact to the bolt 11 attached to the hole (of which position is specified by the specifying device 3) (S705).

Following processing is same as that of the first embodiment. Accordingly, explanation thereof is omitted.

At S701~S702, instead of the hole 12 of the utility pole coated with the coupling agent 9, after a male screw of the sensor 2 (shaped like a bolt) is coated with the coupling agent 9, the sensor 2 may be attached to the hole 12 of the utility pole. Furthermore, instead of this, after the sensor 2 is attached to the hole 12 of the utility pole, the coupling agent 9 may be injected into a gap between the sensor 2 (already attached) and the hole 12 subsequently.

If the coupling agent 9 is injected into a gap between the bolt 11 and the hole 12 of the utility pole, it may be performed together while the coupling agent 9 is being applied to a gap between the sensor 2 and the hole 12 (S701~S702). Alternatively, it may be performed just before the worker applies the impact to the bolt (S705). Furthermore, after the bolt 11 is removed from the utility pole temporarily, and next the hole 12 of the utility port or the male screw of the bolt 11 is coated with the coupling agent 9, then the bolt 11 may be attached to the hole 12 again.

In the deterioration diagnosis method and the deterioration diagnosis system of the second embodiment, by using the coupling agent 9, sensitivity to detect the elastic wave by the sensor 2 can be improved.

Furthermore, when the impact is applied to the bolt 11, a noise component superimposed on the elastic wave can be reduced.

The Third Embodiment

Figure 8A:
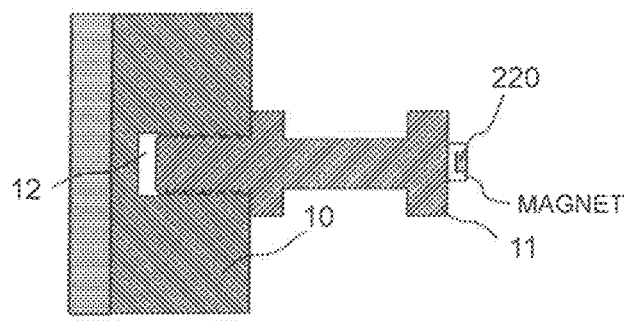
FIGS. 8A and 8B are one example of a detector with a bolt included in the deterioration diagnosis system according to the third embodiment.
Figure 8B:
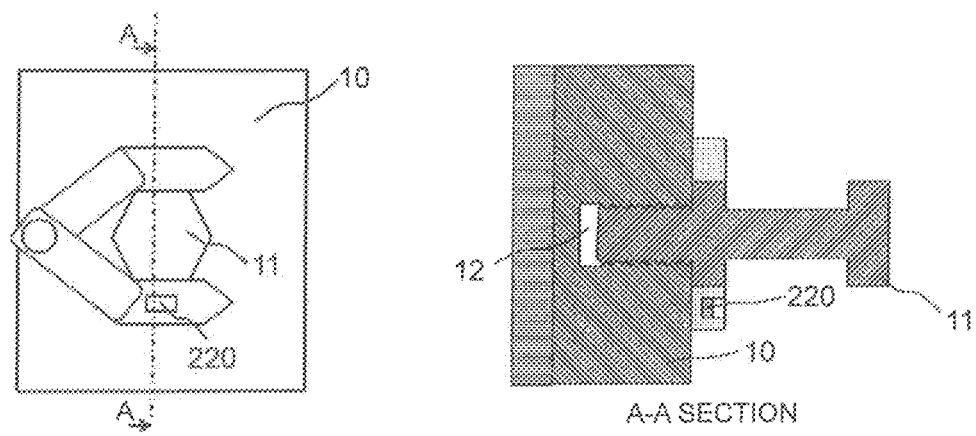

The third embodiment will be explained by referring to FIGS. 8A and 8B. FIGS. 8A and 8B are one example of a detector 220 with a bolt 11 included in the deterioration diagnosis system according to the third embodiment. In the deterioration diagnosis method and the deterioration diagnosis system of the third embodiment, a detector 220 to detect the elastic wave is directly attached to the bolt 11, which is different from the first embodiment. Other components are same as those of the first embodiment.

As shown in FIG. 8A, normally, the bolt is made from iron. Accordingly, by installing a magnet type-attachment mechanism to a housing of the detector, attaching of the detector is easily performed. Furthermore, in order to remove the detector 220 easily from the bolt, the magnet type-attachment mechanism is preferably composed by a switch type-electromagnet. By tightly fixing the detector to the bolt with the electromagnet, the elastic wave can be accurately detected.

Furthermore, FIG. 8B is a frontal view and a sectional view along A-A line in the case that the detector 220 is attached so as to nip the bolt therebetween. As shown in FIG. 8B, in order to improve the measurement sensitivity by adjacently attaching the detector 220 to a main body of the utility pole, the detector 220 may be fixed so as to nip the bolt therebetween. Here, the detector 220 is installed to the housing nipping the bolt.

Figure 9:
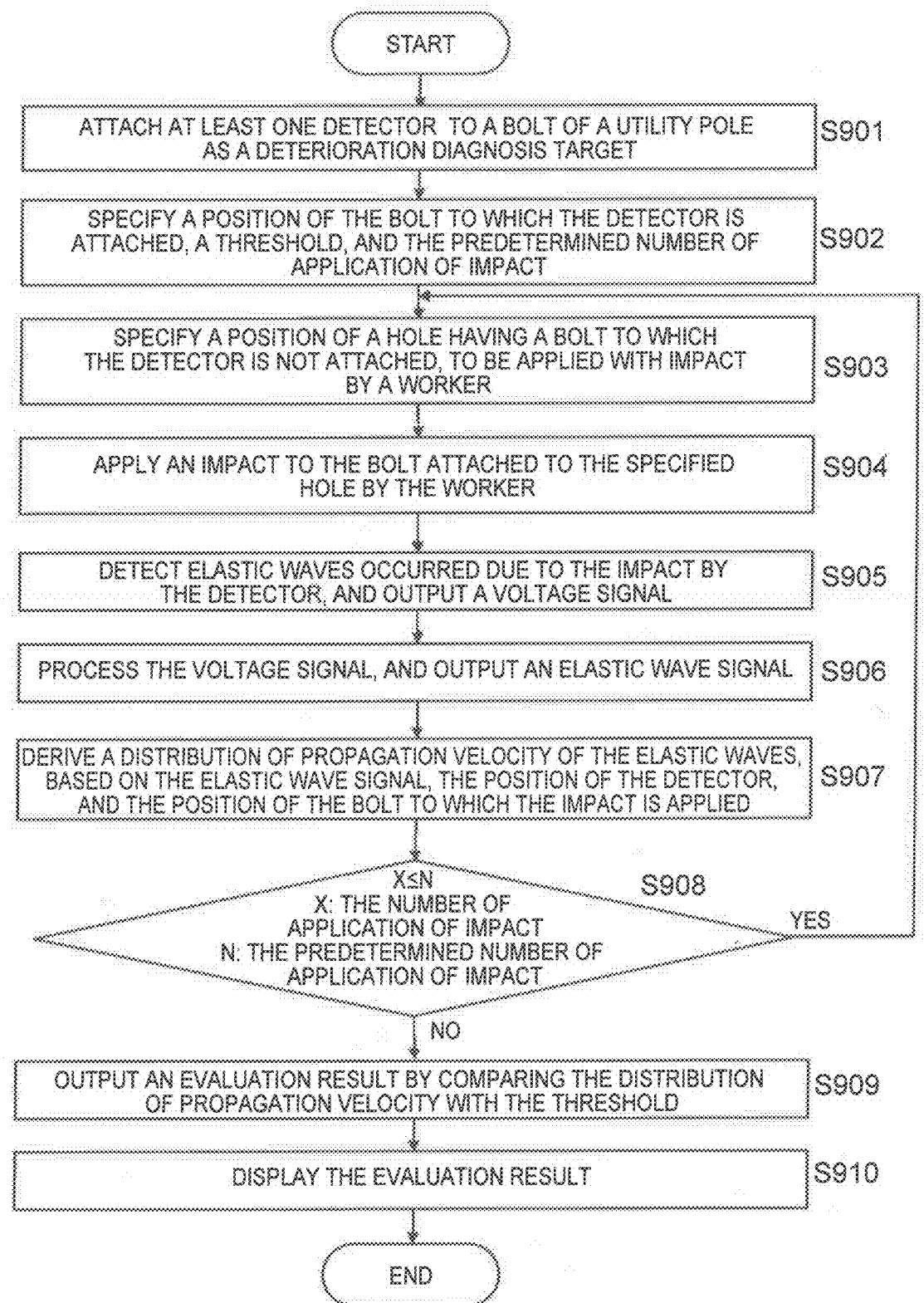
FIG. 9 is a flow chart of processing of the deterioration diagnosis method according to the third embodiment.

FIG. 9 is a flow chart of processing of the deterioration diagnosis method in the case of attaching the detector to the bolt.

First, at least one detector 220 is attached to the bolt of the utility pole as a deterioration diagnosis target. Attaching of the detector 220 to the bolt may be attaching using a magnetic force, or may be attaching so as to nip the bolt (S901).

A position of the hole (to which the bolt having the detector 220 is attached) of the utility pole, and the predetermined number of application of impact (N times), are specified via the specifying device 5. Furthermore, a threshold for the propagation velocity of elastic wave is specified (S902).

The worker specifies a position of the hole (to which the bolt 11 (to be applied with an impact) not having the detector 220 is attached) of the utility pole via the specifying device 5 (S903).

The worker applies the impact to the bolt 11 (not having the detector 220) attached to the hole (of which position is specified by the specifying device 5) (S705).

Following processing is same as that of the first embodiment. Accordingly, explanation thereof is omitted.

In above explanation, the detector 220 is attached by the electromagnet or nipping the bolt therebetween. However, the detector 220 may be pasted to the bolt 11 with adhesive.

In the deterioration diagnosis method and the deterioration diagnosis system of the third embodiment, by directly attaching the detector 220 to the bolt 11, the sensor 2 (shaped like a bolt) need not be attached to the hole of the utility pole. Furthermore, the worker need not remove the bolt 11 to attach the detector 220 thereto. By attaching the detector 220 to the bolt 11 attached to the upper part of the utility pole, the detector 220 can be installed to a position of the upper part of the utility pole.

Furthermore, if the detector 220 is to be attached to the lower part of the utility pole, by attaching a bolt 11 to a hole positioned at the lower part of the utility pole, the detector 220 may be attached to the bolt 11.

In above explanation, the specifying device 5, the storage device 6, and the display device 9, are explained as component of the embodiments. However, these are not necessary components. Any of these components may be omitted.

While certain embodiments have been described, these embodiments have been presented by way of examples only, and are not intended to limit the scope of the inventions. Indeed, the novel embodiments described heroin may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for diagnosing a deterioration of a concrete utility pole having a plurality of holes provided for attaching a bolt as a footing for a worker,
the holes including at least one hole to which the bolt is attached and at least one hole to which the bolt is not attached,
the method comprising:
applying an impact to the bolt;
detecting elastic waves generated due to the impact by a sensor attached to the at least one hole to which the bolt is not attached; and
deriving a propagation situation of the elastic waves in the concrete utility pole, based on the elastic waves detected, and each position of the bolt and the sensor,
wherein the sensor includes:
a housing of which external shape is approximately same as a part of the bolt, the housing being attachable to each of the holes, and
a detector installed to the housing, that detects the elastic waves propagating into the concrete utility pole.

2. The method according to claim 1, wherein
the deriving includes deriving a distribution of propagation velocity of the elastic waves.

3. The method according to claim 2, further comprising:
specifying a threshold; and
evaluating the deterioration of each region of the concrete utility pole by comparing the distribution of propagation velocity or the distribution of attenuation amount with the threshold.

4. The method according to claim 3, wherein
the evaluating includes
evaluating a region of which the distribution of propagation velocity is smaller than the threshold, as the region where the deterioration has progressed, and
evaluating a region of which the distribution of propagation velocity is larger than the threshold, as the region where the deterioration has not progressed.

5. The method according to claim 4, further comprising:
displaying an evaluation result by the evaluating.

6. The method according to claim 1, wherein
the deriving includes deriving a distribution of attenuation amount of amplitude of the elastic eaves.

7. The method according to claim 1, wherein
a female screw is provided for each of the holes,
a male screw is provided for the sensor and the bolt, and
the sensor or the bolt, is attached to the hole by engaging the female screw with the male screw.

8. The method according to claim 1, further comprising:
coating a sealing agent to fill a gap between the sensor and the hole to which the sensor is attached.

9. The method according to claim 1, wherein
the sensor is an AE (Acoustic Emission) sensor.

10. A system for diagnosing a deterioration of a concrete utility pole having a plurality of holes provided for attaching a bolt as a footing for a worker,
the holes including at least one hole to which the bolt is attached and at least one hole to which the bolt is not attached,
the system comprising:
a sensor attached to the at least one hole to which the bolt is not attached, that detects elastic waves generated due to an impact applied to the bolt; and
a derivation device that derives a propagation situation of the elastic waves in the concrete utility pole, based on the elastic waves detected, and each position of the bolt and the sensor,
wherein the sensor includes:
a housing of which external shape is approximately same as a part of the bolt, the housing being attachable to each of the holes, and
a detector installed to the housing, that detects the elastic waves propagating into the concrete utility pole.

11. The system according to claim 10, wherein
the derivation device derives a distribution of propagation velocity of the elastic waves.

12. The system according to claim 11, further comprising:
a specifying device that specifics a threshold; and
an evaluation device that evaluates the deterioration of each region of the concrete utility pole by comparing the distribution of propagation velocity or the distribution of attenuation amount with the threshold.

13. The system according to claim 12, wherein
the evaluation device evaluates a region of which the distribution of propagation velocity is smaller than the threshold as the region where the deterioration has progressed, and evaluates a region of which the distribution of propagation velocity is larger than the threshold as the region where the deterioration has not progressed.

14. The system according to claim 13, further comprising:
a display device that displays an evaluation result by the evaluation device.

15. The system according to claim 10, wherein
the derivation device derives a distribution of attenuation amount of the elastic waves.

16. A sensor used for diagnosis of a concrete utility pole having a plurality of holes to attach a bolt as a footing for a worker,
the holes including at least one hole to which the bolt is attached and at least one hole to which the bolt is not attached,
the sensor comprising:
a housing of which external shape is approximately same as a part of the bolt, the housing being attachable to each of the holes; and
a detector installed to the housing, that detects elastic waves propagating into the concrete utility pole.

17. The sensor according to claim 16, further comprising:
an output part that outputs a detection signal acquired by the detector to outside by a wire or a radio.

18. The sensor according to claim 17, further comprising:
a signal processing part that processes the detection signal.

19. The sensor according to claim 16, wherein
the housing is shaped with a metal.

* * * * *